United States Patent [19]

Rackley

[11] Patent Number: Plant 5,893

[45] Date of Patent: Mar. 3, 1987

[54] PITTOSPORUM PLANT 'LAURALEE'

[76] Inventor: Jon G. Rackley, 1955 Lakeshore Dr., Eustis, Fla. 32726

[21] Appl. No.: 803,676

[22] Filed: Dec. 2, 1985

[51] Int. Cl.[4] ..... A01H 5/00

[52] U.S. Cl. ..... Plt./54

[58] Field of Search ..... Plt./54

[56] References Cited

U.S. PATENT DOCUMENTS

P.P. 4,919 11/1982 Turner ..... Plt./54

P.P. 5,233 5/1984 Turner ..... Plt./54

*Primary Examiner*—James R. Feyrer

*Attorney, Agent, or Firm*—Roger L. Martin

[57] ABSTRACT

A new and distinct variety of Pittosporum plant has many characteristics similar or like those of the 'Wheelerii' variety but is distinguishable therefrom among other things by variegated leaf blade characteristics that provide a basic field on the adaxial side which is marked by spots and blotches that are absent from the field on the abaxial side and by a discontinuous border coloration that is mainly located along the margin of the distal half of the blade and on the abaxial side is a reverse replica of that at the adaxial side of the blade.

9 Drawing Figures

The invention relates to a new and distinct plant vairety of the Pittosporaceae family and which has been name the *Pittosporum tobira* 'Lauralee' by the inventor.

Certain plant varities of the *tobira* species of the Pittosporum genus are well known in the Central Florida market place. Among these are the 'Wheelerii' variety, the 'Variegatum' variety, the 'Compacta' variety and the variety commonly called "Green Pittosporum". The "Green Pittosporum" is believed to be the same variety also known as "Mock-orange" or "Australian laurel". The 'Wheelerii' and 'Compacta' varieties are compact varieties while the 'Variegatum' variety is a variegated plant variety that is substantially larger in growth habit than either of the two compact varieties. The "Green Pittosporum" is also a larger plant than those of the compact varieties and is known to grow to a height of 15–20 feet.

In addition to the four varieties mentioned as being common to the market place, there have been two varieties of the tobia species which have been recently patented but which are not yet available in the market place to the best of the inventor's knowledge. Here reference is made to 'Turner's Dwarf Tricolor' and 'Turner's Dwarf Bi-Color' and which form the subject matters of U.S. Plant Pat. Nos. 5,233 and 4,919, respectively.

The new plant variety forming the subject matter of this application had its origin in a sport or bud variation that made its appearance on a specimen of the 'Wheelerii' variety which was being grown in a nursery at Eustis, Fla. Since its discovery, the new variety has been reproduced asexually by the propagation of stem cuttings at the nursery and through successive propagations it has been ascertained that the new variety has certain reproducable characteristics which will be considered subsequently and which distinguish the new variety from its antecedents and known related varieties.

The new plant variety is distinguishable from *Pittosporum tobira* 'Wheelerii' in several respects. For one, the leaf blades of the 'Wheelerii' variety are not variegated and have a solid green field that lacks the spotted and blotched basic field and the border characteristics found in specimens of the new variety. The 'Wheelerii' variety has a slightly faster growth rate and thus at comparable ages, especially during the first year of growth, produces specimens that are slightly larger than those of the new variety.

The new plant variety is distinguishable from the "Green Pittosporum" in size and leaf variegations among other things. The new variety has a variegated leaf with recognizable characteristics that will be discussed subsequently whereas the "Green Pittosporum" has a solid green field in the leaf blades and lacks variegations. Size-wire the new variety, of course is much smaller and in size its specimens are more comparable to those of the 'Wheelerii' variety.

The variegated variety of *Pittosporum tobira* known as 'Variegatum' is distinguishable from the new variety in the size of the specimens and in the patterns of variegation. Size-wise specimens of the 'Variegatum' variety reach heights of six feet or more whereas specimens of the new variety to date show a clear tendency to follow the height of the 'Wheelerii' variety and thus rarely exceed three feet in height. The patterns of border variegation for the 'Variegatum' variety contemplate both the distal and proximal halves of the blades whereas, with the new variety, the border variegations are usually found in the distal halves of the leaf blades. Apart from the above,the 'Variegatum' variety lacks the spots and blotches that are found in the leaf blades of the new variety and have a pronounced undulating margin in comparison to the nonundulating margins of the new variety.

The 'Compacta' variety of *Pittosporum tobira,* commonly referred to as "Compact Green" or "Pittosporum Compacta" is a compact form of the *tobira* species that has an undulating leaf blade which lacks variegations. It is not as compact as the 'Wheelerii' variety and the specimens frequently grow to a height of 3–4 feet. In contrast to this, the new variety has a growth habit providing shorter and more compact plant specimens than those of the 'Compacta' variety and additionally provides a characteristically variegated leaf blade which, as seen hereinafter, is unlike the 'Compacta' variety an also nonundulating.

The new plant variety is distinguishable in various respects from the variety known as 'Turner's Dwarf Tricolor' and which forms the subject matter of U.S.

Plant Pat. No. 5,233. For one, variegated blades from specimens of this patented variety show a deep penetration of the marginal or border colors into the center blade area in the vast majority of the variegated leaf blades produced whereas by comparison, the border colors of the new variety are confined more to a moderately narrow area along the edges of the blades. In addition the variegated border is usually concentrated in the distal half of the leaf blade in specimens of the new variety whereas the border characteristics usually appear in both the distal and proximal halves of the leaf blades in specimens of the patented variety. The border characteristics are evident in practically all leaves that have been examined on specimens of the new variety to date. Apart from the above differences, specimens of the patented variety are clearly distinguishable from those of the new variety in that they lack the small spots and blotches which are found in the basic fields on the adaxial blade sides of the new variety. These small spots and blotches are noticeably absent from the basic fields at the abaxial blade sides of the new variety while the patented variety has an under surface which is similar to the upper surface but with lighter colors.

The new plant variety is also distinguishable in various respects from the variety known as 'Turner's Dwarf Bi-color' and which forms the subject matter of U.S. Plant Pat. No. 4,919. Specimens of this patented variety also lack the spots and blotches which are found in the basic fields on the adaxial blade sides of the new variety. Such spots and blotches are noticeably absent from the abaxial blade sides of the new variety but again the patented variety has an under surface which is similar to the upper surface but lighter colors. In addition, the border colors of the patented variety penetrate much deeper into the center of the blade than in the new variety. Furthermore, the variegated border is usually concentrated in the distal half of the leaf blade in specimens of the new variety whereas the border characteristics usually appear in both the distal and proximal halves of the leaf blades in specimens of the patented variety.

A general object of the invention has been to develop a compact variety of *Pittosporum tobira* which would be clearly distinguishable from of the other compact varieties of the tobira species and especially from the 'Wheelerii' variety and those closely related thereto. Yet another object has been to develop a compact variety of *Pittosporum tobira* which would be clearly distinguishable from the compact 'Wheelerii' and 'Compacta' varities and others closely related thereto by variegated leaf characteristics that would be consistently reproduced in the leaves developed by asexually reproduced specimens thereof.

The objectives of the invention have been fully realized by the development of the new plant variety described hereafter in detail. Thus, through successive propagations, it has been ascertained that specimens of the new plant variety generally resemble specimens of the dwarf variety, 'Wheelerii', but are distinguishable therefrom and from other related varieties known to the inventor by a growth habit which is evident in specimens propagated and grown at Eustis, Fla. under the conditions set forth hereinafter as combining the following principal characteristics: (1) Posture, compactness and branching tendencies that are comparable to those of the 'Wheelerii' variety, but having a slightly slower growth rate that results in specimens which, during the first year of growth, are evidently slightly smaller in size than specimens of the 'Wheelerii' variety of comparable age. (2) Mature leaf blades which are characteristically variegated and [a] on the adaxial side have a spotted and blotched basic field with a usually moderately narrow and discontinuous border that is mainly located along the margin of the distal half of the leaf blade, and [b] on the abaxial side have a basic field with a notable absence of the spots and blotches found on the adaxial side, but which, nevertheless, has a border that is a reverse replica of that at the adaxial side. (3) The leaf blades contemplated in item (2) above having on the adaxial side [a] a basic field that in color is dominated by yellow green, yellowish green and/or green hues, [b] spots and blotches that are generally darker than the basic field on the adaxial side and in color are dominated by olive green and/or yellowish green hues, and [c] a border that is generally lighter than the basic field on the adaxial side and in color is dominated by yellow green and/or greenish yellow hues. (4) The leaf blades contemplated in item (2) above having on the abaxial side [a] a basic field that in color is dominated by yellowish green and/or yellow green hues, and [b] a border that is generally lighter than the basic field on the abaxial side and in color is dominated by yellow green and/or greenish yellow hues. (5) Consistent reproduction of the variegated leaf blade characteristics in substantially all mature leaves of asexually reproduced specimens of the new plant variety.

The accompanying drawings serve by color photographic means to illustrate the new plant variety and wherein: (1) A first sheet has a side elevational view of a 14 month old specimen of the new plant variety and which is seen as contained in a white plastic pot that is 9½ inches in diameter. (2) A second sheet has a top view of the specimen seen on the first sheet. (3) A third sheet has a top view showing the adaxial sides of the leaves in the apical areas of three branches of the containerized specimen, the apical areas of the three branches being evident in the view on the second sheet and being enlarged to illustrate the initial obscurity or lack of the spots and blotches during early immaturity (<10 days old, e.g. from blade expansion) of the leaves. (4) A fourth sheet has a side view of a primary branch of the containerized specimen and which generally shows the foliage between the apical and basal areas thereof so as to primarily illustrate the nature of the spots and blotches on new mature leaves (>1 month and <12 months old). (5) A fifth sheet has a side view of the apical end of a primary branch of the containerized specimen and which has several secondary branches that are developing during a growth flush at the apical end of this primary branch. (6) A sixth sheet has yet another view of the apical end of the primary branch seen in the view shown on the fifth sheet, the view not only showing the spot and blotch characteristics as the leaves age during the first few months of growth but also showing the characteristic border variegations. (7) A seventh sheet has a view of a portion of a primary branch which was removed from the containerized specimen and broken just distally of a group of transitional leaves that appear on the branch, the view being taken at an acute angle to the axis of the branch and showing the break distally of the transitional leaves as well as some mature nontransitional leaves that are located proximally of the transitional leaves on the branch. (8) An eighth sheet has a view of the adaxial sides of twelve leaves taken from the containerized specimen seen in the view on the first sheet, the four leaves at the left in the view being old mature leaf specimens (>12 months old), the four leaves at the right in the view being immature leaf specimens (<1 month old) and the four leaves in the center of the view being new mature leaf specimens (>1 month and <12 months old). (9) A ninth sheet has a view of the abaxial sides of the twelve leaves seen in the view on the eighth sheet, the leaf specimens being oriented according to age as indicated above.

The following is a detailed description of the new plant variety with colors named in accord with the ISCC-NBS method of designating colors (U.S. Department of Commerce, National Bureau of Standards, Circular 553, issued Nov. 1, 1955) and as interpreted from color notations derived by comparisons with color chips or specimens found in the Munsell Book of Color, published by Munsell Color Macbeth, a division of Kollmorgen Corporation, 2441 N. Calvert Street, Baltimore, Md. 21218.

In the text herein, the designated ISCC-NBC color name is first set forth and then followed in brackets [] with the serial number of the ISCC-NBC color name block therefor. This serial number is, in turn, followed in parenthesis () with the Munsell color notation(s) of hue/value/chroma that were noted in making the color determination.

The description is based on observations of well fertilized plants propagated and grown in the Eustis, Fla. area under the conditions set forth hereinafter. The plants observed for purposes of the plant description were 12-months old at the time of the observations, and the observations including the color comparisons were taken during the months of September and October.

PLANT DESCRIPTION

I. Name: *Pittosporum tobira* 'Lauralee'.

II. Origin: As a sport of *Pittosporum tobira* 'Wheelerii'.

III. Classification:

A. *Botanic.*—1. Family: Pittosporaceae. 2. Genus: Pittosporum. 3. Species: *tobira.*

B. *Commercial.*—Evergreen shrub.

IV. Form: Terrestrial leafy evergreen shrub with branched stems.

V. Plant size (12-14 MOS.):

A. *Height (maximum above ground level).*—Usually 20-47 cm.

B. *Width (maximum horizontal).*—Usually 35-50 cm.

VI. Roots: Adventitious.

VII. Stems and branches:

A. *General.*—Ascending, fruticose, ramiform and adventitiously rootable stems and branches.

B. *Nodes.*—1. General: Short internodal distances with most nodes of 12-14 month old specimens having an attached single subsisting leaf.

2. Internode Distance: Usually less than 7.5 mm. on primary branches of 12-14 month old specimens.

C. *Shapes.*—1. Stems: Elongated and terete. 2. Branches: Elongated and terete.

D. *Stem and branch textures.*—Herbaceous during immaturity and becoming sclerous and woody with age.

E. *Sizes* (12-14 *month old specimens*).—1. Primary Axis: (a) General: Height varies with propagation and potting practices. (b) Height (above soil level). Usually 10-35 mm. with specimens propagated potted and grown as set forth herein. (c) Diameter (at soil level). Usually 9-13 mm. 2. Primary branches: (a) Length. Usually 85-260 mm. (b) Diameter (intermediate insertion and tip). Usually 2-4 mm. 3. Secondary branches: (a) Length. Usually 15-175 mm. (b) Diameter (intermediate insertion and tip). Usually 1.25-2.5 mm.

F. *Stem and branch colors* (12-14 *month old specimens*).—1. General: Branch colors generally darken and approach or become concolorous with those of the primary axis as the branches mature and age. 2. Primary Axes: (a) General. Usually dominated by yellowish brown, olive brown and/or brown hues in both basal and apical areas. (b) Basal Area. Commonly grayish brown [61] (7.5 YR 4/2), light yellowish brown 76] (10 YR 6/4), moderate yellowish brown [77] 10 YR 5/4), light grayish yellowish brown [79] (10 YR 6/2), grayish yellowish brown [80] (10 YR 5/2; 10 YR 4/2), light olive brown [94] (2.5 Y 6/2; 2.5 Y 5/4) and/or moderate olive brown [95] (2.5 Y 4/2). (c) Apical Area. Same as Basal Area. 3. Primary Branches: (a) General: Usually dominated by greenish yellow and/or yellow green hues in the apical areas during the elongation and growth of the stem as part of a growth flush and approaching or becoming concolorous with that of primary axis with age. (b) Basal Area. Commonly light grayish yellowish brown [79] (10 YR 6/2), grayish yellowish brown [80] (10 YR 5/2), grayish yellow [90] (near 2.5 Y 7/2; 2.5 Y 7/4), dark grayish yellow [91] (2.5 Y 6/4; 5 Y 6/4), yellow gray [93] (near 2.5 Y 7/2), light olive brown [94] (2.5 Y 6/2; 2.5 Y 5/4) and/or light olive [106] (5 Y 5/4). (b) Apical Area. Commonly brilliant greenish yellow [98] (near 10 Y 8/8), strong greenish yellow [99] (near 10 Y 8/8; near 10 Y 7/8), deep greenish yellow [100] (near 10 Y 6/8), light greenish yellow [101] (near 10 Y 8/8), moderate greenish yellow [102] (near 10 Y 8/8; near 10 Y 7/8), dark greenish yellow [103] (near 10 Y 6/8), brilliant yellow green [116] (2.5 GY 8/8), strong yellow green [117] (2.5 GY 7/8; 5 GY 7/8), light yellow green [119] (2.5 GY 8/6; 5 GY 8/6; 5 GY 9/6; 2.5 GY 9/6) and/or moderate yellow green [120] (2.5 GY 7/6) during the elongation and growth of the stem as part of a growth flush. 4. Secondary Branches: (a) General. Usually dominated by yellow green hues in the distal areas during the elongation and growth of the the branch as part of a growth flush. (b) Basal Area. Commonly dark grayish yellow [91] (5 Y 6/4), light olive [106] (7.5 Y 6/4; 10 Y 6/4), light yellow green [119] (5 GY 9/6; 2.5 GY 9/6) and/or moderate yellow green [120] (2.5 GY 7/4). (b) Apical Area. Commonly light yellow green [119] (2.5 GY 8/6; 5 GY 8/6; 5 GY 9/6; 2.5 GY 9/6) and/or moderate yellow green [120] (2.5 GY 7/6).

VIII. Leaves:

A. *General.*—Incomplete, exstipulate, petiolate simple leaf with a prominent midrib, and with the frequent occurence between old growth flushes of transitional leaves which are obviously stunted in growth and often deformed.

B. *Leaf shapes.*—1. General: Oblanceolate. 2. Leaf Apicies: Obtuse but frequently showing acute tendencies. 3. Leaf Bases: Attenuate. 4. Leaf Margins: Entire.

C. *Leaf attachments.*—Stalked.

D. *Leaf arrangement.*—Alternate.

E. *Venation.*—1. General: Pinnately netted and reticulodromous with a prominent midrib and secondary, tertiary and lesser veins which are evident under magnification (10×) using transmitted light. 2. Shape and Arrangement: (a) Midrib. Tapering distally and being generally planar on the adaxial side in the basal area of the leaf and keeled at the abaxial side throughout most of its length. (b) Lateral Veins. Secondary, tertiary and lesser veins form a network on each side of the midrib and which is evident under magnification (10×) using transmitted light. (c) Midrib Colors (mature leaves >1 month old). [1] General: Concolorous or nearly concolorous with the petiole colors. [2] Adaxial Side: Commonly light yellow green [119] (5 GY 9/4; 5 GY 8.5/4; 2.5 GY 8.5/4). [3] Abaxial Side: Commonly light yellow green [119] (5 GY 9/4; 5 GY 8.5/4; 2.5 GY 8.5/4).

F. *Petioles.*—1. General: Short and little differentiated from the base of the midrib. 2. Shape: Generally flat to weakly canaliculate and with a channel at the insertion on the adaxial side and keeled on the abaxial side. 3. Petiole Texture: Cartilaginous. 4. Petiole Size (mature nontransitional leaves >1 month old): (a) Length (between insertion and mergence with midrib). Usually 3–8 mm. (b) Diameter (intermediate insertion and mergence with midrib). Usually 1–2 mm. 5. Petiole Color (mature nontransitional leaves >1 month old): (a) General. Concolorous or nearly concolorous with the midrib color and usually dominated by yellow green and/or greenish yellow hues on both adaxial and abaxial sides. (b) Adaxial Side. Commonly brilliant greenish yellow [98] (near 10 Y 8/8), strong greenish yellow [99] (near 10 Y 7/8; near 10 Y 8/8), light greenish yellow [101] (near 10 Y 8/8; 10 Y 8.5/6), moderate greenish yellow [102] (near 10 Y 7/8; near 10 Y 8/8), brilliant yellow green [116] (2.5 GY 9/8; 2.5 GY 8/8), strong yellow green [117] (2.5 GY 7/8), light yellow green [119] (5 GY 9/6; 5 GY 8/6; 5 GY 9/4; 2.5 GY 9/6; 2.5 GY 8.5/6; 2.5 GY 8/6) and/or moderate yellow green [120] (2.5 GY 7/6). (c) Abaxial Side. Commonly brilliant greenish yellow [98] (near 10 Y 8/8), strong greenish yellow [99] (near 10 Y 7/8; near 10 Y 8/8), light greenish yellow [101] (near 10 Y 8/8), moderate greenish yellow [102] (near 10 Y 7/8; near 10 Y 8/8), brilliant yellow green [116] (2.5 GY 8/8), strong yellow green [117] (5 GY 7/8; 2.5 GY 7/8), light yellow green [119] (5 GY 9/6; 5 GY 8.5/6; 5 GY 8/6; 2.5 GY 9/6; 2.5 GY 8/6) and/or moderate yellow green [120] (2.5 GY 7/6).

G. *Leaf blades.*—1. General: The mature blades are characteristically variegated and on the adaxial side there is an evident spotted and blotched basic field that has a usually moderately narrow and discontinuous border which is mainly located along the margin of the distal half of the leaf blade, while on the abaxial side there is a basic field with a notable absence of the spots and blotches but which is nevertheless provided with a border that is a reverse replica (mirror image) of that at the adaxial side.

The spots and blotches are lacking in the embrionic leaves and first become evident as the blades of the immature leaves are expanding or shortly after they become fully expanded, the spots and blotches are somewhat small and obscure initially and remain small but become more distinct and better defined as the blade ages. 2. Blade Texture (Mature leaves >1 month old): Leathery. 3. Blade Sizes (Mature nontransitional leaves>1 month old): (a) Length. Usually 36–76 mm. (b) Width (Maximum). Usually 10–23 mm. 4. Blade Colors (Mature leaves >1 month old): (a) General. On the adaxial side, the basic field in color is dominated by yellow green, yellowish green and/or green hues, the border is generally lighter than the basic field and in color is dominated by yellow green and/or greenish yellow hues, and the spots and blotches are generally darker than the basic field and in color are dominated by olive green and/or yellowish green hues. On the abaxial side, the basic field in color is dominated by yellow green and/or yellowish green hues and the border is generally lighter than the basic field and in color dominated by yellow green and/or greenish yellow hues. (b) Adaxial Side. [1] Basic field: Commonly light yellow green [119] (7.5 GY 8/4), moderate yellow green [120] (2.5 GY 5/4; 2.5 GY 7/4; 5 GY 5/4; 5 GY 6/4; 5 GY 7/4; 7.5 GY 5/4; 7.5 GY 6/4; 7.5 GY 7/4), pale yellow green [121] (7.5 GY 8/2), grayish yellow green [122] (2.5 GY 7/2; 5 GY 6/2; 5 GY 7/2; 7.5 GY 6/2; 7.5 GY 7/2), light yellowish green [135] (10GY 7/4). moderate yellowish green [136] (10 GY 5/4; 10 GY 6/4), and/or pale green [149] (10 GY 7/2). [2] Spots and Blotches: Commonly moderate olive green [125] (2.5 GY 4/4; 5 GY 3/4; 5 GY 4/4; 7.5 GY 3/4; 7.5 GY 4/4; 7.5 GY 4/6), and/or dark yellowish green [137] (10 GY 3/4; 10 GY 4/4; 2.5 G 3/4). [3] Border: Commonly light greenish yellow [101] (near 10 Y 8/6; 10 Y 8.5/6; 10 Y 9/6), moderate greenish yellow [102] (near 10 Y 8/6), brilliant yellow green [116] (2.5 GY 8/8), light yellow green [119] (2.5 GY 8/4; 2.5 GY 8/6; 2.5 GY 8.5/6; 2.5 GY 9/4; 2.5 GY 9/6; 5 GY 8/6; 5 GY 8.5/6; 5 GY 9/4; 5 GY 9/6) and/or moderate yellow green [120] (5 GY 7/4). (c) Abaxial Side. [1] Basic Field: Commonly moderate yellow green [120] (2.5 GY 7/4; 5 GY 6/4; 5 GY 7/4; 7.5 GY 5/4; 7.5 GY 6/4; 7.5 GY 7/4), light yellowish green [135] (10 GY 7/4) and/or moderate yellowish green [136] (10 GY 6/4). [2] Border: Commonly brilliant greenish yellow [98] (near 10 Y 8/8), strong greenish yellow [99] (near 10 Y 7/8; near 10 Y 8/8), light greenish yellow [101] (near 10 Y 8/8; 10 Y 8.5/6; 10 Y 9/6), moderate greenish yellow [102] (near 10 Y 7/8; near 10 Y 8/8), pale greenish yellow [104] (10 Y 9/4), brilliant yellow green [116] (2.5 GY 8/8), strong yellow green [117] (2.5 GY 7/8), light yellow green [119] (2.5 GY 8/4; 2.5 GY 8/6; 2.5 GY 8.5/4; 2.5 GY 8.5/6; 2.5 GY 9/4; 2.5 GY 9/6; 5 GY 9/4; 5 GY 9/6), and/or moderate yellow green [120] (5 GY 7/6).

IX. Flowers: The characteristics of the flower have not been ascertained for reasons of the absence thereof on specimens grown to date.

X. Growth habit: Specimens of the new variety have branching tendencies, as well as posture, and compactness, characteristics that are comparable to specimens of the *Pittosporum tobira* 'Wheelerii' variety. In comparison to the 'Wheelerii' variety, specimens of the new variety exhibit a slightly slower growth rate that results in specimens which during the first year of growth are evidently slightly smaller is size than those of the 'Wheelerii' variety. In addition, the variegated leaf blade patterns indicated heretofore are consistently reproduced in the leaves developed on asexually reproduced specimens of the new variety, there having been substantially no evidence to date of reversion back to the solid green field of the 'Wheelerii'.

Propagation and Growing Procedure

The propogation and growing procedures followed in reproducing the new variety and in growing the specimens from which the above "PLANT DESCRIPTION" and the below "Description of Plant Specimen" have been developed may be illustrated by reference to the procedures utilized in propogating specimens from the first specimen of the new variety which was developed from the sport or bud variation appearing on the parent plant of the 'Wheelerii' variety.

In carrying out the propogations, semi-hardwood tip cuttings from 7 to 10 cm long were removed from primary branches of the specimen and the leaves from the lower one-third length of the cutting were manually stripped from the cutting. These cuttings were then individually stuck to a depth comparable with that of the stripped length and without special treatment in a "propogating media" that was supported in a cavity, 40 mm. in diameter and 75 mm. deep, of conventional growing trays used in the nursery industry for propogation purposes. The media consisted of a 1:1 volume mixture of Canadian peat and horticultural perlite.

The propagating procedure transpired in the middle of August and for the next 10 weeks, the cuttings were subjected to conditions in a conventional open air, full sun, mist house where they were under an intermittent mist of 5 sec. every 4 min. during sunny weather conditions. The average low and high temperature conditions during the months involved were August: 69°-92° F.; September: 66°-88° F.; October 61°-86° F.

At the end of the 10 week period, the trays containing the rooted cuttings were placed in a 30% shaded polyethylene greenhouse until the middle of the following March so as to harden out and become more environmentally acclimated. During this period the plants were watered every second day and fertilized once with a slow release 18-6-12 ($N$-$P_2O_5$-$K_2O$) fertilizer.

At the end of the hardening period and in March of the year following propagation, each of the rooted cuttings was transplanted to a black plastic container, 25 cm. in diameter and 25 cm. deep, containing a growing media consisting of a 2:4:1 volume mixture of Canadian peat, ground southern pine bark and coarse sand, the media having been modified by the admixture therewith on a cubic yard basis and in finely divided form of 680 gm. of a trace element fertilizer mixture, 2.3 kg. of dolomite and 4.5 kg. of a slow release 18-6-12 ($N$-$P_2O_5$-$K_2O$) fertilizer. In transplanting the rooted cuttings, the propogating media containing the roots was covered with the growing media to a depth of 25-30 mm.

Following the transplant the specimens were retained in a fabric shade house providing 35% shade and allowed to grow without pruning until examined during the months of September and October for purposes of this application. Throughout their residency in the shade house, the specimens were provided an average of 1.0 cm. of water and 100 ppm. of nitrogen from an 8-0-6 ($N$-$P_2O_5$-$K_2O$) source every other day and also subjected to routine pest control measures.

The "trace element fertilizer mixture" referred to above had a reported elemental analysis of: S (12%), B (0.1%), Cu (0.5%), Fe (12.0%), Mn (2.5%) Mo (0.05%) and Zn (1.0%) and wherein the elements are derived from sodium borate, copper sulfate, ferrous sulfate, manganese sulfate, sodium molybdate and zinc sulfate.

All of the procedures described herein were carried out in the Eustis, Fla. area, including the propagating, transplanting and growing procedures.

Description of Plant Specimen

The following is a general description of a specimen of the new plant variety that was propagated, transplanted and grown under the conditions indicated above at Eustis, Fla., the description having been taken during October.

I. General:
- A. *Age of plant.*—14 months.
- B. *Month of description.*—October.

II. Plant size:
- A. *Crown height (maximum above grown level)*.—26.5 cm.
- B. *Crown height (average)*.—19 cm.
- C. *Width (maximum horizontal dimension)*.—47 cm.
- D. *Width (minimum horizontal dimension)*.—37 cm.

III Stems and branches:
- A. *No. of primary branches.*—13.
- B. *No. of secondary branches.*—7.
- C. *Sizes.*—See Table I below.
- D. *Colors.*—1. Primary Axis: (a) Basal Area. Grayish yellowish brown [80] (10 YR 4/2), grayish brown [61] (7.5 YR 4/2) and moderate olive brown [95] (2.5 Y 4/2). (b) Apical Area. Grayish yellowish brown [80] (10 YR 4/2), grayish brown [61] (7.5 YR 4/2) and moderate olive brown [95] (2.5 Y 4/2). 2. Primary Branches: (a) Basal Area. Dark grayish yellow [91] (2.5 Y 6/4; 5 Y 6/4), light olive brown [94] (2.5 Y 5/4) and light olive [106] (5 Y 5/4). (b) Apical Area. Brilliant yellow green [116] (2.5 GY 8/8), strong yellow green [117] (2.5 GY 7/8), light yellow green [119] (2.5 GY 8/6; 5 GY 8/6) and moderate yellow green [120] (2.5 GY 7/6). 3. Secondary Branches: (a) Basal Area. Dark grayish yellow [91] (5 Y 6/4), light olive [106] (7.5 Y 6/4; 10 Y 6/4) and moderate yellow green [120] (2.5 GY 7/4). (b) Apical Area. Light yellow [86] (near 2.5 Y 8/6), moderate yellow [87] (near 2.5 Y 8/6, light yellow green [119] (5 GY 8/6) and moderate yellow green [120] (2.5 GY 7/4).

IV. Leaves:
- A. *Mature leaf distribution.*—See Table II.
- B. *Petioles.*—1. Petiole size (mature nontransitional leaves): (a) On Primary Axis. [1] Length: 7 mm. (av.). [2] Diameter: 1.6 mm. (av.). (b) On Primary Branches. [1] Length: 4.6 mm. (av.). [2] Diameter: 1.2 mm. (av.). (c) On Secondary Branches. [1] Length: 4.5 mm. (av.). [2] Diameter: 1.3 mm. (av.). 2. Petiole color (mature leaves >1 month old): (a) On Primary Axis. [1] Adaxial Side: Brilliant greenish yellow [98] (near 10 Y 8/8), strong greenish yellow [99] (near 10 Y 7/8; near 10 Y 8/8), light greenish yellow [101] (near 10 Y 8/8), moderate greenish yellow [102] (near 10 Y 7/8; near 10 Y 8/8). brilliant yellow green [116] (2.5 GY 8/8; 2.5 GY 9/8) and light yellow green [119] (5 GY 9/6). [2] Abaxial Side: Strong greenish yellow [99] (near 10 Y 7/8), moderate greenish yellow [102] (near 10 Y 7/8), strong yellow green [117] (2.5 GY 7/8; 5 GY 7/8) and light yellow green [119] (2.5 GY 8/6; 5 GY 8/6). (b) On Primary Branches. [1] Adaxial Side: Light yellow green [119] (2.5 GY 8.5/6; 2.5 GY 9/6; 5 GY 8/6; 5 GY 9/4; 5 GY 9/6). [2] Abaxial Side: Brilliant yellow green [116] (2.5 GY 8/8) and light yellow green [119] (2.5 GY 8/6; 5 GY 8/6; 5 GY 8.5/6; 5 GY 9/6). (c) On Secondary Branches. [1] Adaxial Side: Light yellow green [119] (2.5 GY 8/6; 5 GY 8/6). [2] Abaxial Side: Brilliant yellow green [116] (2.5 GY 8/8), strong yellow green [117] (2.5 GY 7/8), light yellow green [119] (2.5 GY 8/6; 5 GY 8.5/6; 5 GY 8/6) and moderate yellow green [120] (2.5 GY 7/6). 3. Leaf Blades (Mature nontransitional leaves): (a) Sizes. [1] On Primary Axis: [a] Length (incl. petiole). 62.3 mm. (av.). [b] Width (maximum). 18.7 mm. (av.). [2] On Primary Branches: [a] Length (incl. petiole). 44.6 mm. (av.). [b] Width (maximum). 15.3 mm. (av.). [3] On Secondary Branches: [a] Length (incl. petiole). 54 mm. (av.). [b] Width (maximum. 17.2 mm. (av.). (b) Color. [1] On Primary Axis: [a] Adaxial Side. 1-Basic field: Moderate yellow green [120] (2.5 GY 7/4; 5 GY 7/4; 7.5 GY 6/4; 7.5 GY 7/4), light yellowish green [135] (10 GY 7/4) and moderate yellowish green [136] (10 GY 6/4). 2-Spots and Blotches: Moderate olive green [125] (2.5 GY 4/4; 5 GY 4/4; 7.5 GY 3/4; 7.5 GY 4/4) and dark yellowish green [137] (10 GY 3/4; 10 GY 4/4). 3-Border: Light yellow green [119] (2.5 GY 9/6; 5 GY 9/6). [b] Abaxial Side. 1-Basic Fields: Moderate yellow green [120] (2.5 GY 7/4; 5 GY 6/4; 7.5 GY 6/4; 7.5 GY 7/4), light yellowish green [135] (10 GY 7/4) and moderate yellowish green [136] (10 GY 6/4). 2-Border: Brilliant greenish yellow [98] (near 10 Y 8/8), strong greenish yellow [99] (near 10 Y 7/8; near 10 Y 8/8), light greenish yellow [101] (near 10 Y 8/8), moderate greenish yellow [102] (near 10 Y 7/8; near 10 Y 8/8) and light yellow green [119] (2.5 GY 8/6). (2) On Primary Branches: [a] Adaxial Side. 1-Basic Field: Moderate yellow green [120] (2.5 GY 5/4; 5 GY 5/4; 7.5 GY 5/4). 2-Spots and Blotches: Moderate olive green [125] (5 GY 4/4; 7.5 GY 3/4; 7.5 GY 4/4). 3-Border: Brilliant yellow green [116] (2.5 GY 8/8) and light yellow green [119] (2.5 GY 8/6; 2.5 GY 9/6). [b] Abaxial Side. 1-Basic Field: Moderate yellow green [120] (5 GY 6/4; 7.5 GY 5/4; 7.5 GY 6/4). 2-Border: Light greenish yellow [101] (10 Y 9/6), pale greenish yellow [104] (10 Y 9/4) and light yellow green [119] (2.5 GY 8/4; 2.5 GY 8/6; 2.5 GY 9/4; 2.5 GY 9/6). (3) On Secondary Branches: [a] Adaxial Side. 1-Basic Field: Moderate yellow green [120] (5 GY 5/4; 7.5 GY 5/4). 2-Spots and Blotches: Moderate olive green [125] (5 GY 4/4; 7.5 GY 4/4). 3-Border: Light yellow green [119] (2.5 GY 8/6; 2.5 GY 9/6), light greenish yellow [101] (near 10 Y 8/6) and moderate greenish yellow [102] (near 10 Y 8/6). [b] Abaxial Side. 1-Basic Field: Moderate yellow green [120] (5 GY 6/4). 2-Border: Light greenish yellow [101] (10 Y 9/6) and light yellow green [119] (2.5 GY 8/4; 2.5 GY 9/6).

TABLE I

STEM AND BRANCH SIZES

| Stem/Branch I.D. | Height/Length mm.(1) | Diameter mm.(2) |
|---|---|---|
| Primary Axis | 28 | 11 |
| Primary Branches | | |
| #1 | 233 | 3.5 |
| #2 | 187 | 3.0 |
| #3 | 200 | 4.0 |
| #4 | 245 | 4.0 |
| #5 | 113 | 3.0 |
| #6 | 86 | 3.0 |
| #7 | 256 | 3.5 |
| #8 | 198 | 4.0 |
| #9 | 207 | 3.5 |
| #10 | 212 | 3.5 |
| #11 | 125 | 2.0 |
| #12 | 113 | 3.0 |
| #13 | 94 | 3.0 |
| Secondary Branches | | |
| #1 | 160 | 2.5 |
| #2 | 28 | 1.5 |
| #3 | 16 | 1.5 |
| #4 | 25 | 1.5 |
| #5 | 39 | 1.5 |
| #6 | 131 | 2.0 |
| #7 | 122 | 2.5 |

(1)Height of primary axis is measured above soil level whereas lengths of branches are measured as distances between the tips and insertions of the branches.
(2)Diameter of primary axis is measured at soil level whereas diameters of branches are measured generally intermediate the tips and insertions of the branches.

TABLE II

MATURE LEAF DISTRIBUTION

| Stem/Branch I.D. | No. of Leaves(1) | Stem/Branch I.D. | Leaves(1) |
|---|---|---|---|
| Primary Axis | 10 | Primary Branch | |
| Primary Branch | | #11 | 9 |
| #1 | 73 | #12 | 24 |
| #2 | 36 | #13 | 61 |
| #3 | 64 | Secondary Branch | |
| #4 | 80 | #1 | 18 |
| #5 | 26 | #2 | 0 |
| #6 | 32 | #3 | 0 |
| #7 | 70 | #4 | 0 |
| #8 | 77 | #5 | 0 |
| #9 | 60 | #6 | 13 |
| #10 | 46 | #7 | 15 |

(1)Fully expanded nontransitional mature leaves >1 mos. old.

I claim:

1. The new and distinct variety of *Pittosporum* plant substantially as herein shown and described and which is principally distinguishable by a growth habit that combines the following characteristics:

(a) Posture, compactness and branching characteristics that are comparable to those of the 'Wheelerii' variety, (b) A slightly slower growth rate than exibited by the 'Wheelerii' variety and which results, during the first year of growth, in specimens that are evidently slightly smaller in sizes than specimens of comparable age of the 'Wheelerii' variety, (c) Mature leaf blades which are characteristically variegated and [1] on the adaxial side have a spotted and blotched basic field with a usually moderately narrow and discontinuous border which is mainly located along the margin of the distal half of the leaf blade, and [2] on the abaxial side have a basic field with a notable absence of the spots and blotches found on the adaxial side, but which has a border that is a reverse replica of that at the adaxial side of the blade, (d) The leaf blades contemplated in item (c) having on the adaxial side [1] a basic field that, in color, is dominated by yellow green, yellowish green and/or green hues, [2] spots and blotches which are generally darker than the basic field on the adaxial side and, in color, are dominated by olive green and/or yellowish green hues, and [3] a border which is generally lighter than the basic field on the adaxial side and, in color, is dominated by yellow green and/or greenish yellow hues, (e) The leaf blades contemplated in item (c) having on the abaxial aide [1] a basic field that, in color, is dominated by yellowish green and/or yellow green hues, and [2] a border that is generally lighter than the basic field on the abaxial side and, in color, is dominated by yellow green and/or greenish yellow hues, (f) Consistent reproduction of the variegated leaf blade characteristics in substantially all mature leaves of asexually reproduced specimens of the new variety.

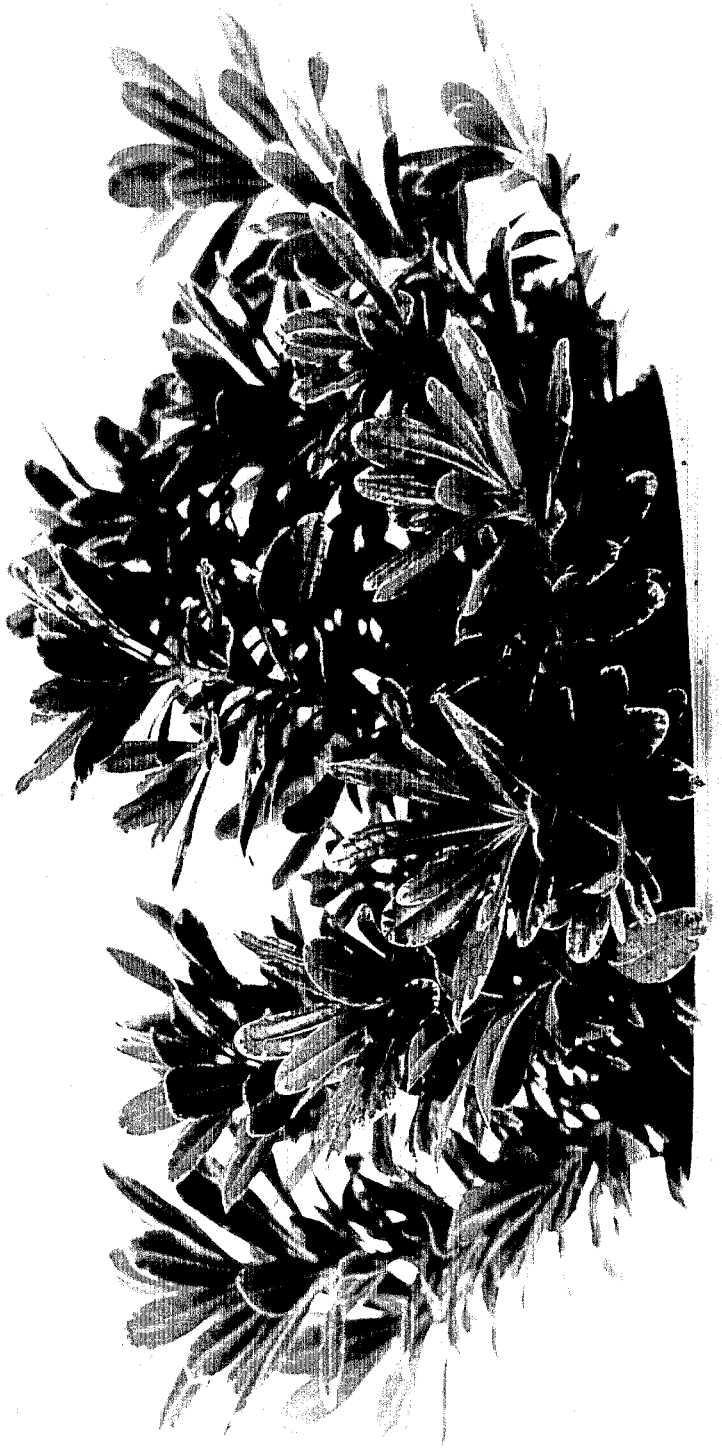

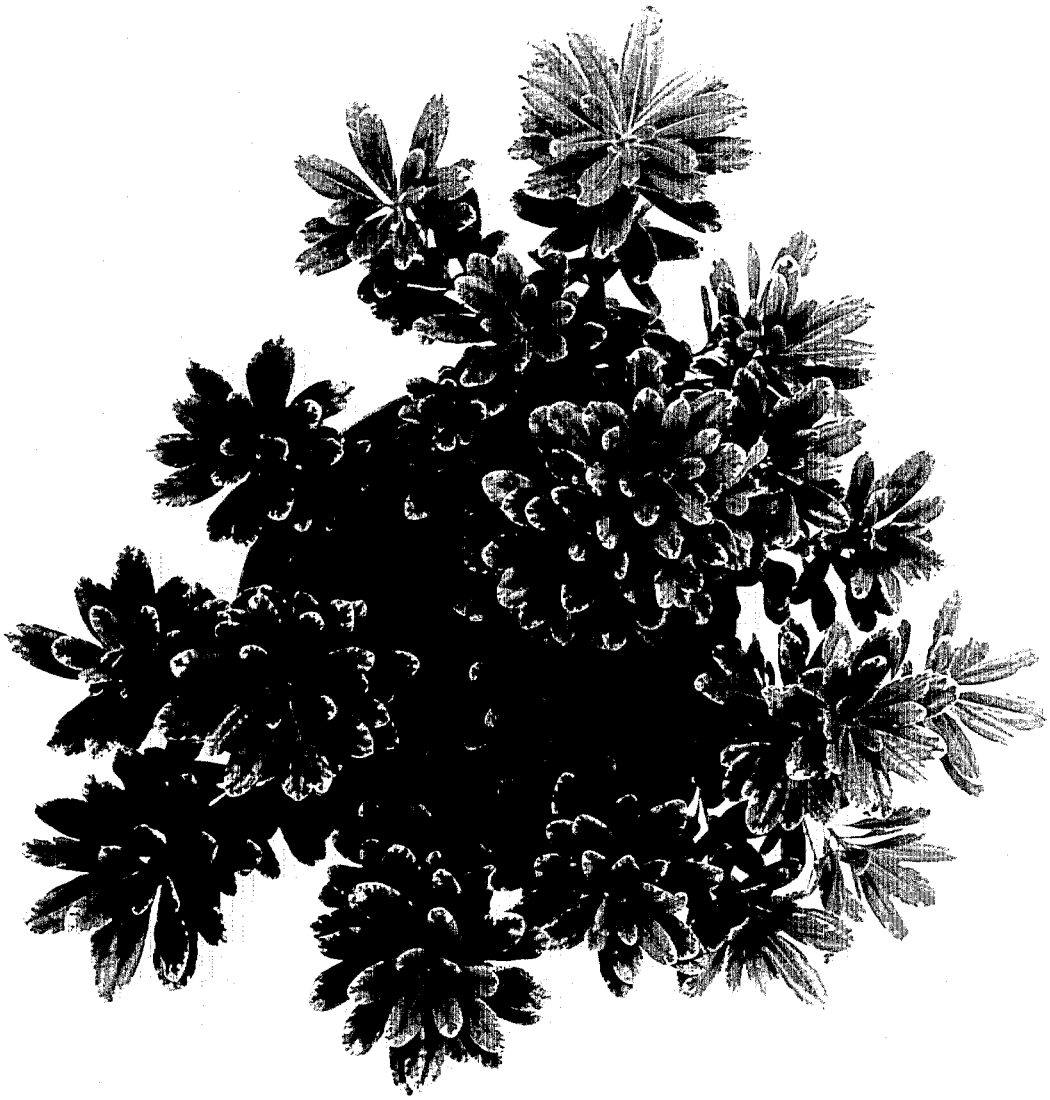

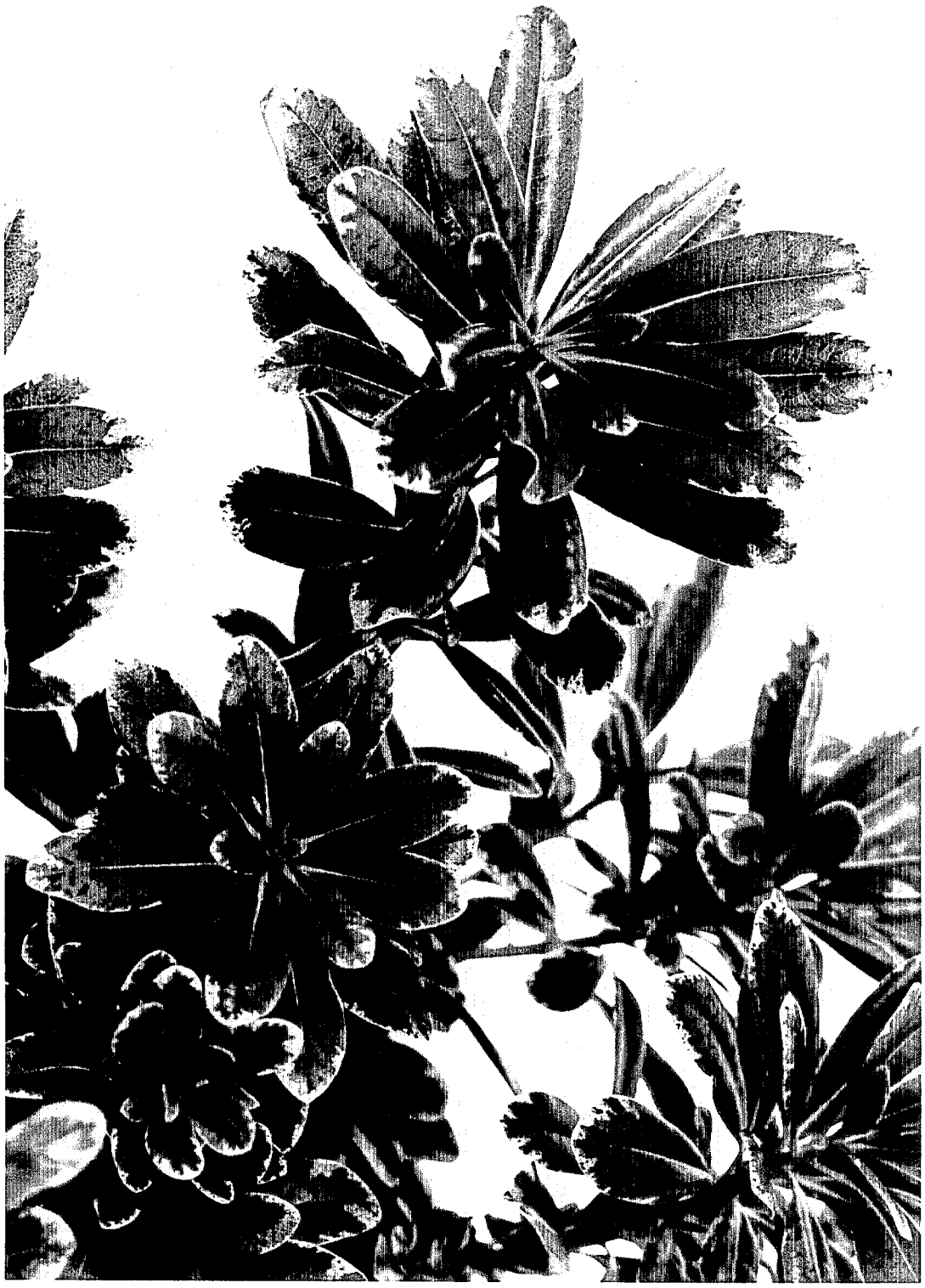

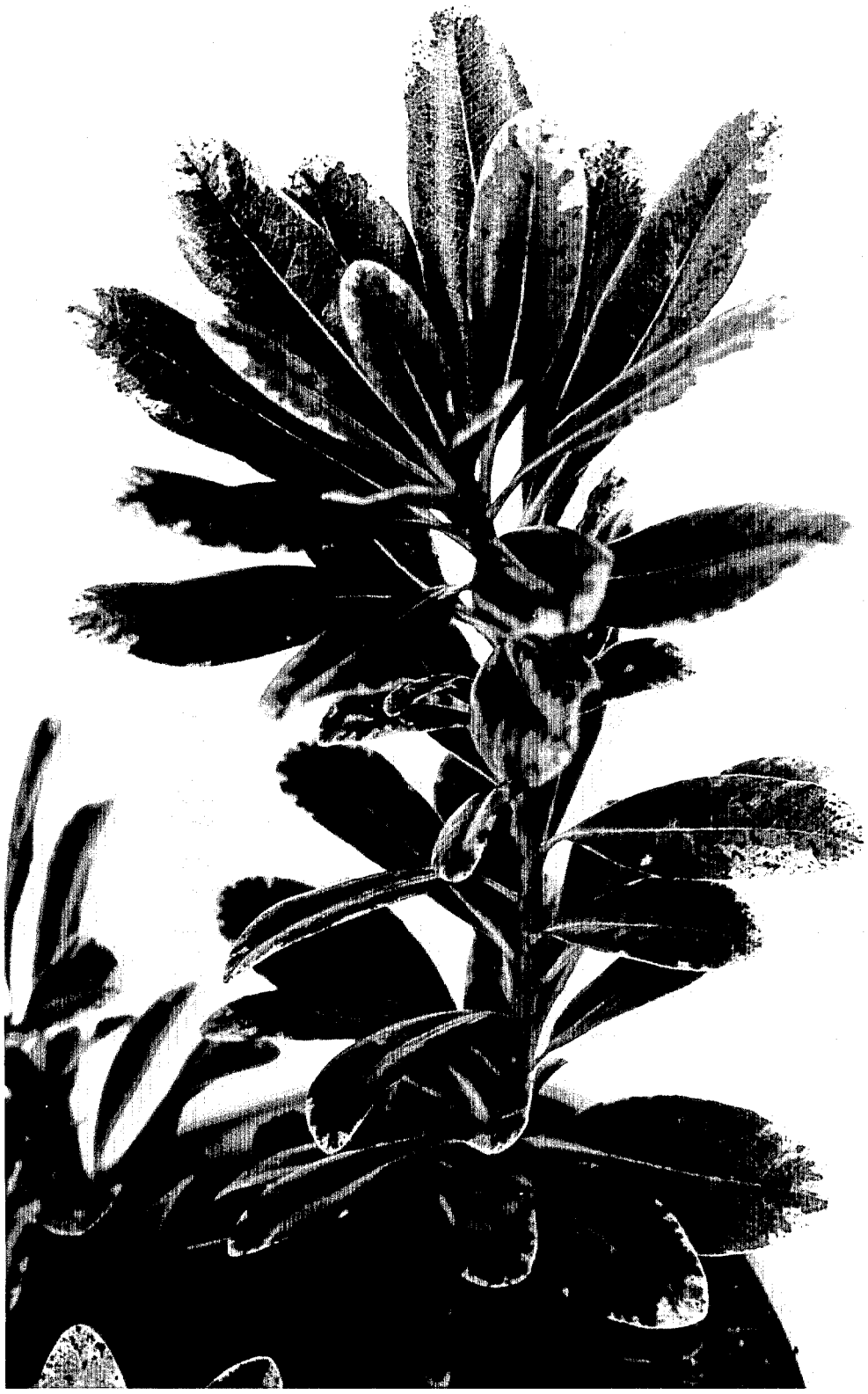

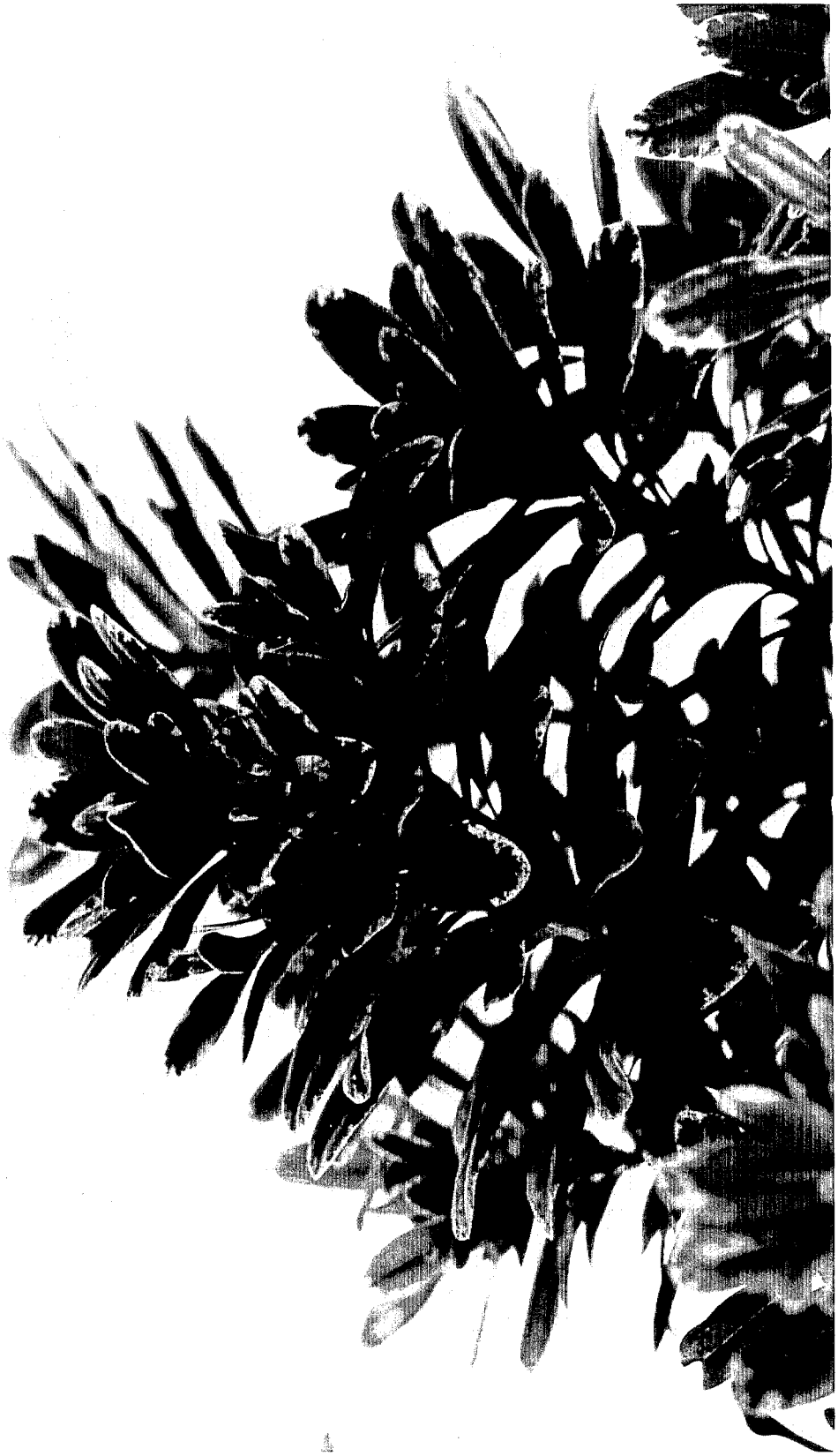

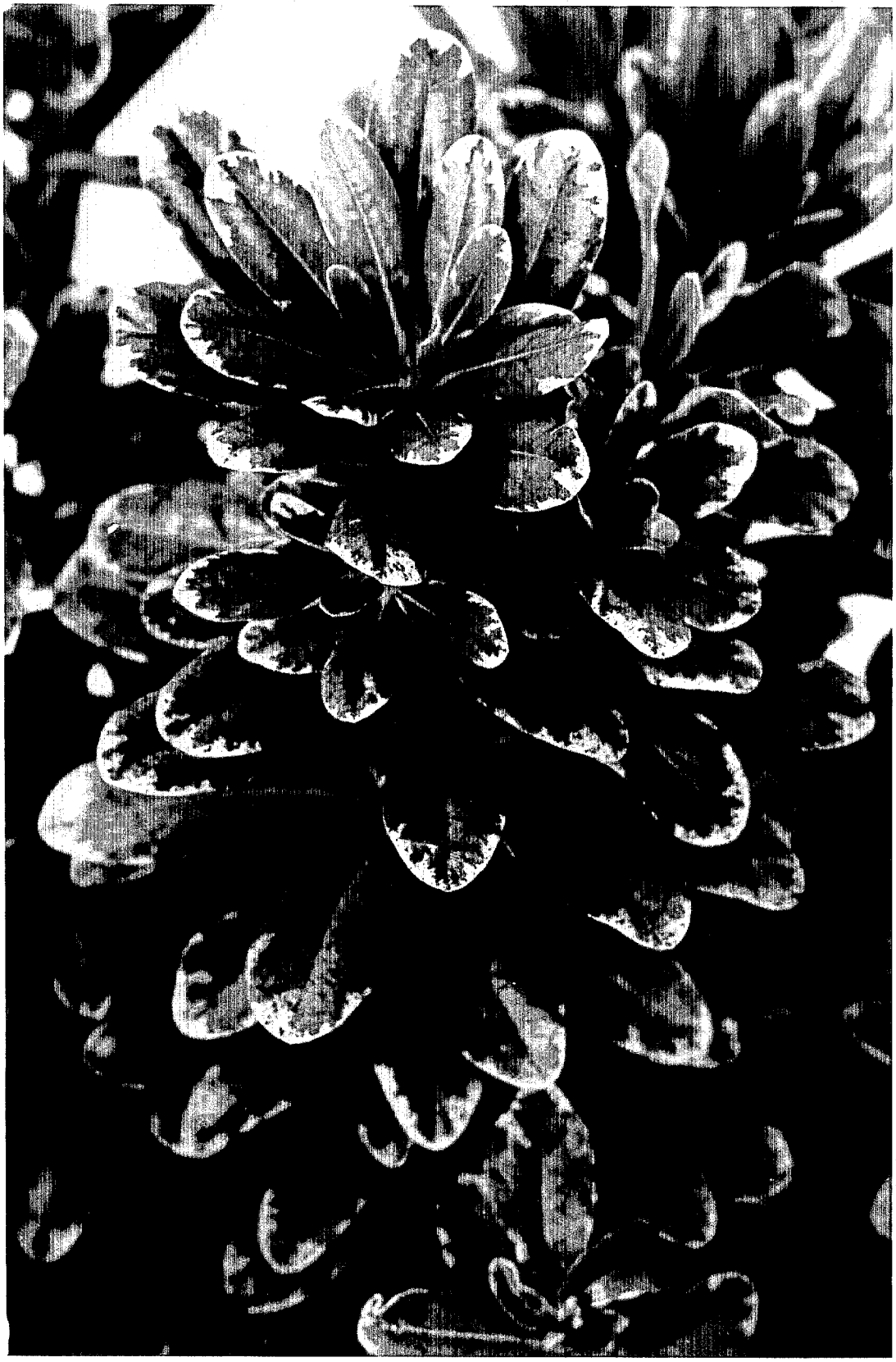

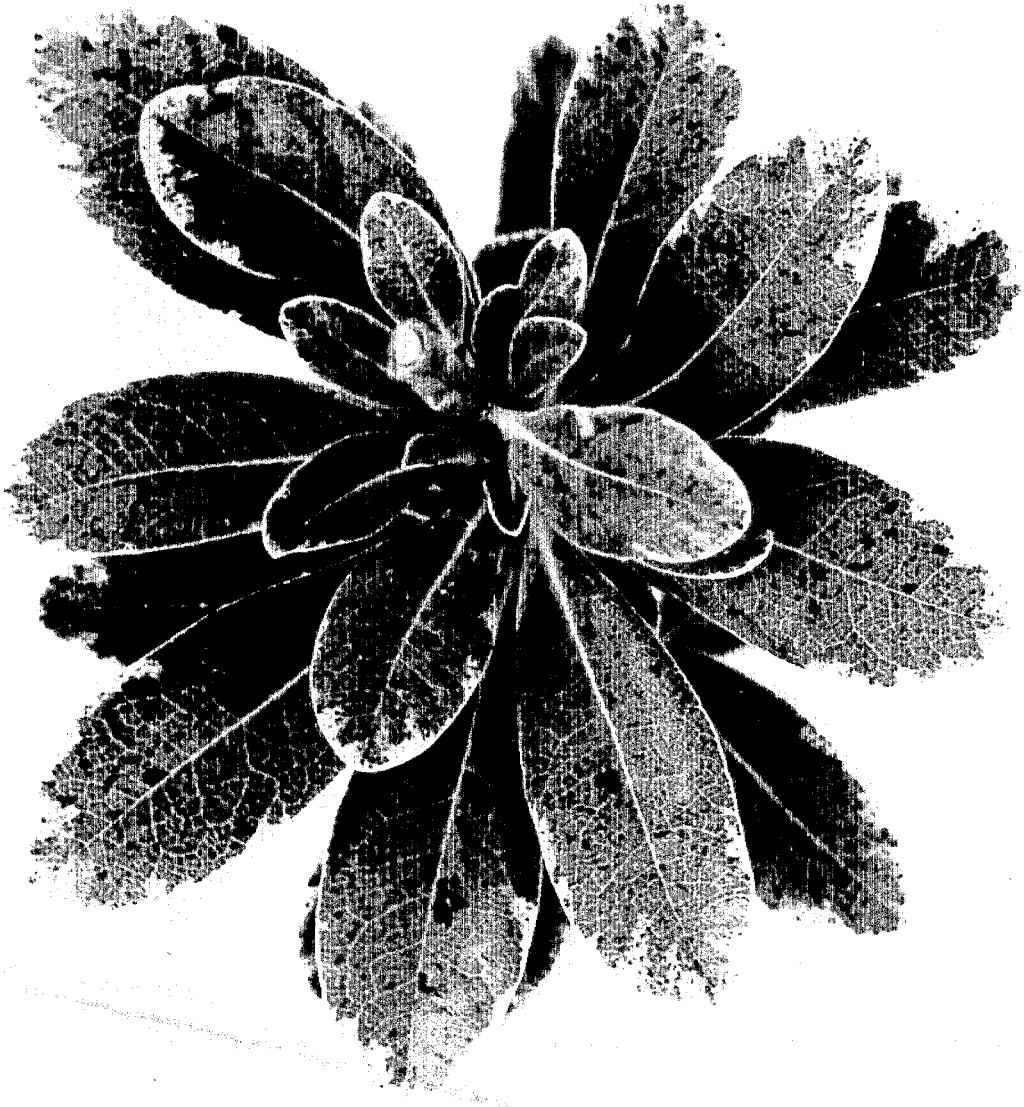

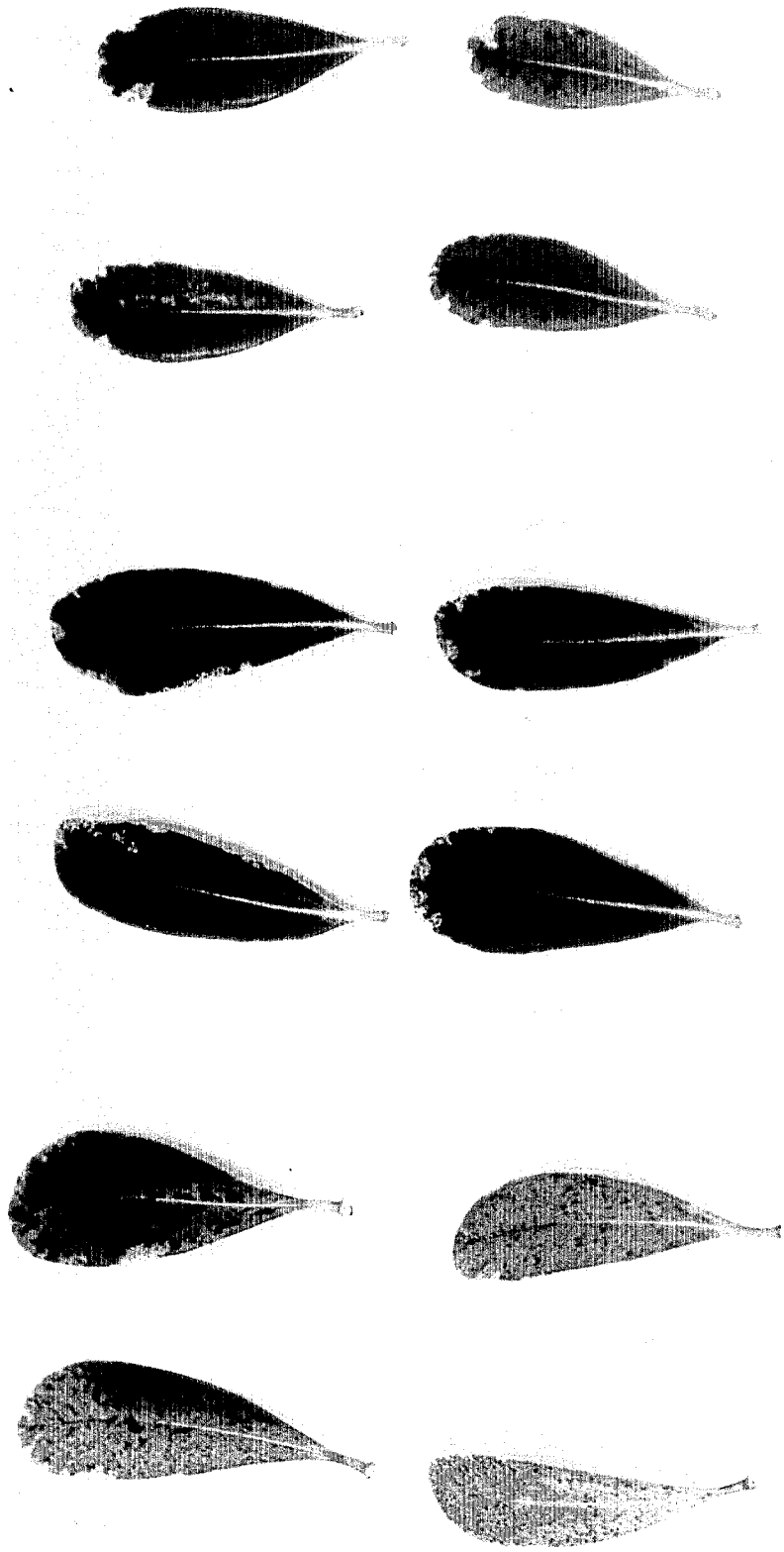

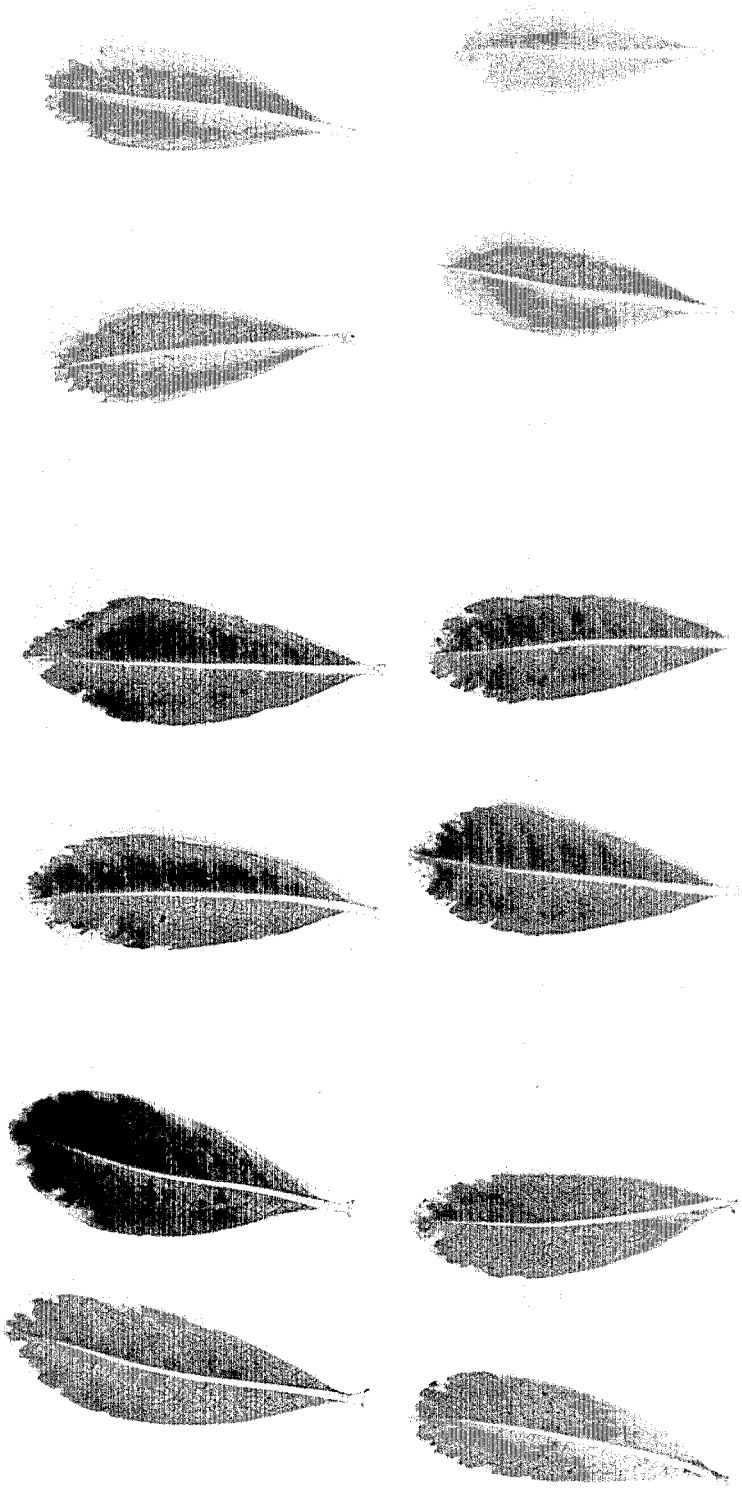

* * * * *